United States Patent [19]

Gaffar

[11] 4,188,372

[45] Feb. 12, 1980

[54] ANTIBACTERIAL ORAL COMPOSITION

[75] Inventor: Abdul Gaffar, Somerset, N.J.

[73] Assignee: Colgate-Palmolive Company, New York, N.Y.

[21] Appl. No.: 938,678

[22] Filed: Aug. 31, 1978

Related U.S. Application Data

[63] Continuation of Ser. No. 754,651, Dec. 27, 1976, abandoned.

[51] Int. Cl.$^2$ .......................... A61K 7/16; A61K 7/18; A61K 7/22; A61K 7/24
[52] U.S. Cl. ........................................ 424/54; 424/49; 424/52; 424/55; 424/57
[58] Field of Search ..................................... 424/54, 55

[56] References Cited

U.S. PATENT DOCUMENTS

| | | | |
|---|---|---|---|
| 3,542,917 | 11/1970 | Schwartz | 424/49 |
| 3,671,626 | 6/1972 | Felger | 424/49 |
| 3,920,837 | 11/1975 | Schmidt-Donker et al. | 424/49 X |

FOREIGN PATENT DOCUMENTS 2411383  9/1974  Fed. Rep. of Germany .

*Primary Examiner*—Shep K. Rose
*Attorney, Agent, or Firm*—H. S. Sylvester; M. M. Grill; R. L. Stone

[57] ABSTRACT

An antibacterial oral composition effective to promote oral hygiene containing a quaternary ammonium antibacterial antiplaque agent and an additive which reduces staining of dental surfaces without substantially diminishing the antibacterial and antiplaque activity of the agent. Benzethonium chloride and cetyl pyridinium chloride, are typical examples of such antibacterial agents. The antistain additive is mellitic acid, 1,2,3,4,5,6-hexahydromellitic acid and/or an orally acceptable salt thereof.

16 Claims, No Drawings

ANTIBACTERIAL ORAL COMPOSITION

This is a continuation of application Ser. No. 754,651 filed Dec. 27, 1976, now abandoned.

This invention relates to an antibacterial oral composition which promotes oral hygiene.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2, p. 632-635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial and antiplaque quaternary ammonium compounds is benzethonium chloride, also known as Hyamine 1622 or diisobutylphenoxyethoxyethyl dimethyl benzyl ammonium chloride. In an oral preparation this material is highly effective in promoting oral hygiene by reducing formation of dental plaque and calculus, which is generally accompanied by a reduction in caries formation and periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, dodecyl dimethyl (2-phenoxyethyl) ammonium bromide, benzyl dimethyl stearyl ammonium chloride, cetyl pyridinium chloride and quaternized 5-amino-1,3-bis(2-ethyl-hexyl)-5-methyl hexa hydropyrimidine are other typical quaternary ammonium antibacterial agents.

The long chain tertiary amines also possess antibacterial and antiplaque activity. Such antibacterial agents include tertiary amines having one fatty alkyl group (typically 12 to 18 carbon atoms) and 2 poly(oxyethylene) groups attached to the nitrogen (typically containing a total from 2 to 50 ethenoxy groups per molecule) and salts thereof with acids and compounds of the structure:

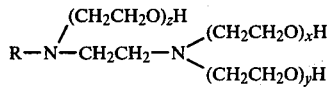

where R is a fatty alkyl group containing 12 to 18 carbon atoms, and x, y and z total 3 or higher, as well as salts thereof. Generally, cationic agents are preferred for their antiplaque effectiveness.

The antibacterial antiplaque compound is preferably one which has an antibacterial activity such that its phenol coefficient is well over 50, more preferably well above 100, such as above about 200 or more for *S. aureus*; for instance the phenol co-efficient (A.O.A.C.) of benzethonium chloride is given by the manufacturer as 410, for *S. aureus*. The cationic antibacterial agent will generally be a monomeric (or possibly dimeric) material molecular weight well below 2,000, such as less than about 1,000. It is however, within the broader scope of the invention to employ a polymeric cationic antibacteria agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The cationic quaternary ammonium and long chain tertiary amine antibacterial agents effectively promote oral hygiene, particularly by removing plaque. However, their use has been observed to lead to staining of dental surfaces or discoloration.

The reason for the formation of such dental stain has not been clearly established. However, human dental enamel contains a high proportion (about 95%) of hydroxyapatite which includes $Ca^{+2}$ and $PO_4^{-3}$ ions. In the absence of dental plaque additional $Ca^{+2}$ and $PO_4^{-3}$, particularly from saliva, can be deposited on the enamel and such deposits can include color bodies which ultimately stain the tooth enamel as a calcified deposit thereon. It can be that as the cationic quaternary ammonium or long chain tertiary amine antibacterial agents remove plaque they also denature protein from saliva in the oral environment and the denatured protein can then act as a nucleating agent which is deposited on and stains or discolors tooth enamel.

Previously employed additives which reduced dental staining by cationic antibacterial antiplaque agents also generally reduced the activity of the antibacterial agents or its ability to act on dental plaque to measurable degrees. Further Victamide (also known as Victamine C) which is the condensation product of ammonia with phosphorus pentoxide actually increases staining even in the absence of a cationic antibacterial antiplaque agent and it and other known phosphorus containing agents such as disodiumethane-1-hydroxy-1,1-diphosphonic acid salt precipitate in the presence of antibacterial agent such as bis-biguanido compound, thereby reducing the antiplaque effectiveness of the antibacterial agent.

British Patent 1,319,396 and corresponding German Pat. No. 2,161,477 recommend the use of pyromellitic acid (benzene 1,2,4,5-tetracarboxylic acid) to prevent staining and buildup of plaque on teeth, corresponding U.S. Pat. No. 3,671,626 peculiarly omitting any mention of a stain-preventing function. These patents disclose optional concurrent use of conventional oral additives including preservatives and germicides, among which quaternary ammonium compounds are mentioned, but no indication is provided concerning the staining of teeth by quaternary ammonium antiplaque antibacterial agents, much less a means for reducing or preventing such staining.

French Pat. No. 2,220,270 recommends the use of cyclic organic carboxylic acids, including melletic acid and other benzene carboxylic acids, to prevent or reduce hydroxyapatite-containing plaque, optional with other conventional additives including therapeutic agents such as bis-biguanides, but without referring to staining of teeth by such bis-biguanides, much less a means for reducing or preventing such staining. Further, mellitic acid precipitates and/or forms an insoluble complex with bis-biguanides, thereby pro tanto reducing the latter's antiplaque activity.

U.S. Pat. No. 3,920,837 is directed to a method of treating calcium disorders, including buildup of tartar or hydroxyapatite crystals on the teeth, using cyclohexane hexacarboxylic acid, but without mentioning antistaining functions, or use in conjunction with any antiplaque antibacterial agent.

It is an advantage of this invention that an antinucleating additive is provided which prevents staining of dental enamel without precipitating or substantially adversely affecting the antibacterial and antiplaque activity of a cationic quaternary ammonium or long chain tertiary amine antibacterial agents. Other advantages will be apparent from consideration of the following disclosure.

In accordance with certain of its aspects this invention relates to an oral composition comprising an oral vehicle, at least one cationic quaternary ammonium or long chain tertiary amine antibacterial antiplaque agent and as an additive thereto mellitic acid (benzene hexacarboxylic acid) or hexahydromellitic acid (cyclohexane hexacarboxylic acid) or mixtures thereof, including orally acceptable salts thereof, for example those containing such cations as alkali metal (e.g. sodium and potassium), ammonium, $C_{1-18}$ mono-, di- and tri- substituted ammonium (e.g. alkanol substituted such as mono-, di- and tri- ethanolammonium), amine, etc. These additives in their free acid form are water soluble, as are their orally acceptable salts operative herein.

The concentration of these mellitic acid additives in oral compositions can range widely, typically upward from about 0.005% by weight with no upper limit except as dictated by cost or incompatibility with the vehicle. Generally, concentrations from about 0.005% to about 10% and preferably about 0.01% to about 2% by weight are utilized. Oral compositions which in the ordinary course of usage could be accidentally ingested preferably contain lower concentrations of these additives. Thus, a mouthwash in accordance with this invention preferably contains less than about 1% by weight of the additive. Dentifice compositions, topical solutions and prophylactic pastes, the latter to be administered professionally can preferably contain about 0.1% to 2%, by weight of the additive. Most desirably, the mellitic acid additive is present in a molar ratio relative to the amount of antibacterial antiplaque agent (based on its free base) of about 0.2:1 to about 6:1, preferably about 0.5:1 to about 4:1, in order to best minimize, inhibit or prevent staining.

Antibacterial agents which are cationic quaternary ammonium or long chain tertiary amine germicides which may be employed in the practice of this invention are described above. They are typically employed in amounts such that the oral product contains between about 0.001% and 15% by weight of the agent. Preferably for desired levels of antiplaque effect, the finished oral product contains about 0.01 to about 5%, and most preferably about 0.025% to 1.0% by weight of the antibacterial agent, referring to its free base form.

The stain which generally occurs on dental enamel is unexpectedly substantially or entirely prevented when the above-defined mellitic acid additives or orally acceptable water soluble salts thereof, are employed. These materials are anti-nucleating agents. In themselves (even in the absence of cationic antiplaque antibacterial agents) they are effective to reduce formation of dental calculus without unduly decalcifying enamel. However, not all anti-nucleating agents are effective to prevent stain by cationic antibacterial agents. For instance, Victamide actually increases staining even in the absence of an antibacterial antiplaque agent.

In certain highly preferred forms of the invention the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water alcohol mixture in this type of preparation is typically in the range of from about 70% to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 $cm^2/gm$. silica gel, complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metalaluminosilicate complexes are particularly useful, since they have refractive indices close to the refractive indices of gelling agent-liquid (including water and/or humectant) systems commonly used in dentifrices.

Many of the so called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than 1% of the material is larger than 37 microns.

The polishing material is generally present in amounts ranging from about 20% to about 99% by weight of the oral preparation. Preferably, it is present in amounts ranging from about 20% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antibacterial antiplaque agent and melliticcontaining compound should be compatible with the other components of the preparation. Thus, in a toothpaste, the liquid vehicle may comprise water and humectant typically in an amount ranging from about 10% to about 90% by weight of the preparation. Glycerine, sorbitol, or polyethylene glycol may also be presented as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gumlike materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead tube.

The solid or pasty oral preparation which typically has a pH measured on a 20% slurry of about 4.5 to 9, generally about 5.5 to about 8 and preferably about 6 to above 8.0, may also contain a surface active agent and-/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral composition such as mouthrinses and toothpastes, a surfactant is often present, e.g. to promote foaming. It will be understood that it is preferable to employ nonionic surfactants rather than their anionic counterparts. Examples of water-soluble nonionic surfactants are condensation products of ethyleneoxide with various compounds reactive therewith having long hydrophobic chains (e.g. aliphatic chains of 12 to 20 carbon atoms) which condensation products ("ethoxamers") have hydrophilic polyoxy ethylene moieties, such as condensation products of ethylene oxide and fatty acids, fatty alcohols, fatty amides, including alcohols such as sorbitan monostearate or polypropylene oxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a thin fluoride such as stannic fluoride or stannous chlorofluoride, barium fluoride, sodium fluorsilicate, ammonium flurosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of 1% by weight of the preparation is considered satisfactory. Any suitable minimum amount of such compound may be used, but it is preferable to employ sufficient compound to release from 0.005%, to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight, more typically 0.76%.

In a liquid oral preparation such as a mouthwash, the fluorine-providing compound is typically present in an amount sufficient to release up to 0.13%, preferably from 0.0013% to 0.1% and most preferably from 0.003% to 0.05%, by weight, of fluoride ion.

Various other materials may be incorporated in the oral preparations of this invention. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and saccharine. Suitably, flavor and sweetening agents may together comprise from 0.01% to 5% or more of the preparation.

In preparing the oral compositions of this invention comprising the above-defined combination of antibacterial agent and mellitic-containing compound in an oral vehicle which typically includes water, it is highly preferred if not essential to add the mellitic-containing compound after the other ingredients (except perhaps some of the water) are mixed or contacted with each other to avoid a tendency for said agent to be precipitated.

For instance, a mouthrinse or mouthwash may be prepared by mixing ethanol and water with flavoring oil, nonionic surfactant, humectant, cationic antibacterial antiplaque agent, such as benzethonium chloride, or cetyl pyridinium chloride, sweetener, color and then the above-defined mellitic acid-containing compound, followed by additional water as desired.

A toothpaste may be prepared by forming a gel with humectant, gum or thickener such as hydroxyethyl cellulose, sweetener and adding thereto polishing agent, flavor, antibacterial agent, additional water, and then the above-defined mellitic acid-containing compound. If sodium carboxymethyl cellulose is employed as the gelling agent the procedure of either U.S. Pat. No. 3,842,168 or U.S. Pat. No. 3,843,779, modified by the inclusion of the mellitic acid-containing compound is followed.

In the practice of this invention an oral composition according to this invention, such as mouthwash or toothpaste containing cationic quaternary ammonium or long chain amine antibacterial antiplaque agent in an amount effective to promote oral hygiene and the defined mellitic acid-containing compound in an amount effective to reduce staining of dental surfaces otherwise resulting from the presence of the antibacterial antiplaque agent, is applied regularly to dental enamel, preferably from about 5 times per week to about 3 times daily, at a pH of about 4.5 to about 9, generally about 5.5 to about 8, preferably about 6 to 8.

The following specific examples are further illustrative of the nature of the present invention, but it is understood that the invention is not limited thereto. All amounts and proportions referred to herein and in the appended claims are by weight unless otherwise indicated. In the examples, BC means benzethonium chloride, CPC means cetyl pyridinium chloride, and MA means mellitic acid.

separated, dried and color levels (in reflectance units) determine on a Gardner Color Difference Meter before and after the test composition is applied to the colored material.

The above results plainly establish that mellitic acid substantially reduces dental staining ordinarily produced by quaternary ammonium antibacterial antiplaque agents as exemplified by BC and CPC. Formulations adjusted to pH 5-8 yield similar results. Orally acceptable salts of mellitic acid yield similar results. Further, tests for antiplaque activity vs. actinomyces viscosus indicate formulations 3 and 4 (BC and MA) to be equivalent to 2 (BC), and formulation 6 (CPC and MA) to be equivalent to 5 (CPC).

EXAMPLES 7-9

Substitution of equivalent amounts of hexahydro mellitic acid for the MA in Examples 3, 4 and 6 yield similar results.

EXAMPLES 10-12

Similar results are obtained when the BC and CPC of Examples 3, 4 and 6 are substituted by an equivalent amount of the long chain tertiary amine antibacterial antiplaque agent of the formula:

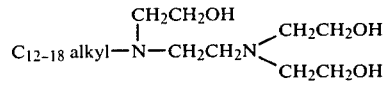

The following formulations exemplify toothpastes with anti-plaque activity and reduced staining:

|  | Example (Parts) | |
| --- | --- | --- |
|  | 13 | 14 |
| Hydrated alumina | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Benzethonium chloride (BC) | 0.5 | — |
| CPC | — | 4.725 |
| MA | 2 | 2 |
| Sodium saccharin | 0.17 | 0.17 |
| Flavor | 0.8 | 0.8 |
| Water q.s. to | 100 | 100 |

TABLE I

| | MOUTHWASH FORMULATIONS | | | | | |
| --- | --- | --- | --- | --- | --- | --- |
| | EXAMPLE | | | | | |
| | (1) Placebo | (2) Control | (3) | (4) | (5) Control | (6) |
| Flavor | 0.22% | 0.22% | 0.22% | 0.22% | 0.22% | 0.22% |
| Ethanol | 15.0 | 15.0 | 15.0 | 15.0 | 15.0 | 15.0 |
| BC | — | 0.075 | 0.075 | 0.075 | — | — |
| CPC | — | — | — | — | 0.1 | 0.1 |
| Pluronic F108* | 3.0 | 3.0 | 3.0 | 3.0 | 3.0 | 3.0 |
| Glycerin | 10.0 | 10.0 | 10.0 | 10.0 | 10.0 | 10.0 |
| MA | — | — | 0.1 | 0.5 | — | 0.2 |
| Water qs to pH 7.0 (with NaOH) | 100 | 100 | 100 | 100 | 100 | 100 |
| Appearance | clear | clear | clear | clear | clear | clear |
| Reflectance | 56 | 48 | 52 | 56 | 31 | 38 |
| Reflectance Difference | — | — | 4 | 8 | — | 71 |

*polyalkene oxide block polymer

The MA, and about 10 parts of the water, are added to the other previously mixed ingredients. Tooth staining characteristics are tested by slurrying hydroxyapatite (Biogel) with salivary protein and acetaldehyde and a pH 7 phosphate buffer. The mixture is shaken at 37° C. until a light brown color is formed. Colored powder is This invention has been described with respect to preferred embodiments and it will be understood that modifications and variations thereof obvious to those skilled in the art are to be included within the spirit and purview of this application and the scope of the appended claims.

What is claimed is:

1. An oral composition comprising an oral vehicle, at least one nitrogen-containing antibacterial antiplaque agent selected from the group consisting of cationic quaternary ammonium antibacterial antiplaque agent and long chain tertiary amine antibacterial antiplaque agent containing a fatty alkyl group of 12 to 18 carbon atoms, and mellitic acid or hexahydromellitic acid as an antistain additive.

2. The oral composition of claim 1 wherein said antibacterial antiplaque agent is present in an amount to provide about 0.001% to about 15% by weight based on the free base form of said agent and said antistain additive is present in amount of about 0.005% to about 10% by weight.

3. The oral composition of claim 2 wherein said antibacterial antiplaque agent is present in an amount of about 0.01% to about 5% by weight, based on its free base form, and said additive is present in a molar ratio relative to said agent of about 0.2:1 to about 6:1.

4. The oral composition of claim 2 wherein said antibacterial antiplaque agent is $C_{12-18}$ alkyl tertiary amine.

5. The oral composition of claim 4 wherein said antibacterial antiplaque agent has the formula

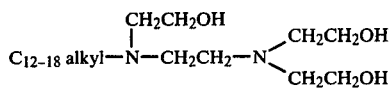

6. The oral composition of claim 2 wherein said antibacterial antiplaque agent is a quaternary ammonium compound.

7. The oral composition of claim 6 wherein said antibacterial antiplaque agent is benzethonium chloride.

8. The oral composition of claim 6 wherein said antibacterial antiplaque agent is cetyl pyridinium chloride.

9. The oral composition of claim 1 wherein said additive is mellitic acid.

10. The oral composition of claim 1 wherein said additive is hexahydromellitic acid.

11. The oral composition of claim 1 wherein said vehicle is an aqueous-alcohol and said composition is a mouthwash of pH of about 4.5 to about 9.

12. The oral composition of claim 1 wherein said vehicle comprises a liquid vehicle and a gelling agent and a dentally acceptable polishing material is present and said composition is a toothpaste of pH of about 4.5 to about 9.

13. The mouthwash composition of claim 11 containing about 0.01% to about 5.0% by weight, based on its free base form, of benzethonium chloride and said additive is present in a molar ratio relative to said benzethonium chloride of about 0.2:1 to about 6:1.

14. The mouthwash composition of claim 11 containing about 0.01% to about 5% by weight, based on its free base form, of cetylpyridinium chloride and said additive is present in a molar ratio relative to said cetyl pyridinium chloride of about 0.2:1 to about 6:1.

15. A method of preparing an oral composition as defined in claim 1 wherein said additive is added to the remaining components of said composition after said components have been contacted with each other.

16. A method of improving oral hygiene comprising applying to the oral cavity an effective amount of an oral composition as defined in claim 1.

* * * * *